United States Patent [19]

Dutta et al.

[11] Patent Number: 5,223,782
[45] Date of Patent: Jun. 29, 1993

[54] METHOD FOR MEASURING THE FLUIDITY OF FLUIDIZED BEDS

[75] Inventors: Arunava Dutta, Chestnut Hill; Leonard V. Dullea, Peabody, both of Mass.

[73] Assignee: GTE Products Corporation, Stamford, Conn.

[21] Appl. No.: 750,783

[22] Filed: Aug. 27, 1991

[51] Int. Cl.⁵ ............................................. G01N 27/04
[52] U.S. Cl. ................................. 324/71.1; 324/452; 73/28.01
[58] Field of Search ............... 324/452, 453, 454, 71.1; 73/28.01

[56] References Cited

U.S. PATENT DOCUMENTS

| | | | |
|---|---|---|---|
| 3,753,102 | 8/1973 | Beck | 324/453 X |
| 3,784,902 | 1/1974 | Huber | 324/454 X |
| 4,261,109 | 4/1981 | Mikus et al. | 324/204 X |
| 4,275,353 | 6/1981 | Yang et al. | 324/459 |
| 4,710,674 | 12/1987 | Sigai | 313/489 |
| 4,779,163 | 10/1988 | Bickford et al. | 324/454 X |
| 4,973,909 | 11/1990 | Castle et al. | 324/452 |
| 5,095,275 | 3/1992 | Dechene et al. | 324/454 |

OTHER PUBLICATIONS

Dutta, A. and L. V. Dullea, AIChE Symp. Ser. #276 (vol. 86), 26 (Jan. 1990).
Dutta, A. and L. V. Dullea, "Effects of the Addition of Highly Dispersed Alumina on the Cohesivity and Fluidization of Group C" presented at the AIChE Ann. Mtg., Pap. #163f, Washington, D.C. Nov. (1988).
Kunii & Levenspiel, "Fluidization Engineering", Krieger Pub., Chp. 5, Jan. 1977.

Primary Examiner—Jack B. Harvey
Assistant Examiner—Glenn W. Brown
Attorney, Agent, or Firm—Robert E. Walter

[57] ABSTRACT

In a method for detecting the fluidity of particles in a vertically extending bed of fluidized particles, an electric charge which is generated on the particles is dissipated through an electrically conductive means in the fluidized bed to give an indication of the fluidity of the particles in the bed.

14 Claims, 5 Drawing Sheets

METHOD FOR MEASURING THE FLUIDITY OF FLUIDIZED BEDS

FIELD OF THE INVENTION

The present invention relates to fluidized beds where upwardly flowing gases are introduced into the bottom portion of a container to fluidize particles therein.

BACKGROUND OF THE INVENTION

The fluidity of a powder processing bed is an important parameter for quality control. There is strong economic incentive to measure the fluidity during processing. It allows time for any remedial control action, thereby preventing the formation of an off-specification product at the end of the run.

The fluidity of a phosphor fluid bed depends on the inherent cohesiveness of the material, the fluidizing gas flow rate, and the spatial distribution of gas in the bed volume. The cohesiveness of phosphors is well documented, and researchers have found various additives which, when blended with the phosphor in optimum amounts, reduce the inherent cohesiveness of the phosphor. Techniques of determining bed fluidity, however, have deficiencies. Current methods rely on visual observation of the bed, measurements of bed expansion, elutriation loss, and normalized bed pressure drop.

While visual observation of the bed is probably the best nonquantitative method of estimating the bed fluidity, it requires a transparent wall material for the fluid bed. This restricts the wall to materials like quartz and high temperature glasses which can stand the elevated temperatures needed for gas/solid reactions in the bed. Since these materials have the severe handicap of being brittle, a major safety hazard is introduced into industrial processes, especially when the chemicals being processed in the fluid bed are pyrophoric. An example of such a chemical is trimethyl aluminum whose use is discussed in U.S. Pat. No. 4,678,970.

It should be noted that bed expansion by itself is not a complete and definite measure of bed fluidity. In fluidization of cohesive powders, like phosphors for example, the bed may expand simply due to the presence of multiple cracks in the bed, without displaying significant powder movement. Bed expansion measurements for estimation of bed fluidity should be complemented by measurements of elutriation loss and/or normalized bed pressure drop.

One can physically measure the bed expansion using a scale on the external wall of the fluid bed. This would require a transparent wall, with its associated safety disadvantage. One can also measure bed expansion using ultrasonic sensors located in the freeboard. The accuracy of these units is often questionable due to interference of the signal by the presence of a powder dust cloud in the freeboard. X-ray bed level detection systems are sometimes used, but several industries prefer not to adopt radiation methods for health reasons.

Other parameters remaining the same, a higher elutriation loss results from a more mobile fluid bed system than from one where the powder movement is slight. Measurements of elutriation loss involve weighing the mass of powder lost from the bed over a certain period of time. While this is feasible in a laboratory process, industrial processes in which flammable and/or pyrophoric chemicals are being used are less suited for such measurements. It can generally be said that a treatment which increases both the bed expansion and the elutriation loss makes the bed more fluid. This means that if several different concentrations of an additive were being tested for their effect on bed fluidity, that treatment which gave the highest bed expansion and the highest elutriation loss could be considered as producing the most mobile bed. Elutriation losses are not desired, however, in industrial processing, especially when expensive powders are being handled. It is possible to minimize bed material loss, without sacrificing bed expansion, by suitable design of the freeboard section.

In a gas fluidized bed with no channeling, almost all of the bed weight is supported by the pressure drop of the gas. This is typically the case in gas fluidization of Geldart type B and A materials. As one moves to finer materials, however, gas channeling starts, bubbles disappear and are largely replaced by a network of vertical and inclined cracks. Under these conditions the ratio of bed pressure drop to bed material weight, often referred to as the normalized bed pressure drop, is less than unity. Bed fluidity decreases as the normalized bed pressure drop deviates more from unity. The bed mass used in the calculation refers to the initial mass of material charged to the bed.

Direct measurement of bed pressure drop is easily accomplished for Geldart type A and B materials, by installing one or more pressure transducers just above the distributor plate. A similar procedure is problematic for Geldart Class C materials (like phosphors) because any screen like device used to isolate the sensor from the bed material is easily clogged by the fine particles. For these materials, the bed pressure drop is usually found by installing a pressure transducer in the plenum section of the fluid bed. This provides the total pressure drop during actual operation, and the distributor pressure drop when gas is passed through the plate with no bed present. Subtraction of the latter data from the former yields the bed pressure drop. It is possible to develop a computer based system to calculate in real time the bed pressure drop and the normalized bed pressure drop.

A problem with this method of determining bed pressure drop occurs when one or more of the precursor chemicals used in the CVD reactions in the bed is prone to pyrolysis. Pyrolysis, or thermal decomposition in the absence of oxygen, at the distributor plate can lead to partial plugging of the pores of the plate. The distributor plate pressure drop is an increasing function of gas flow rate per unit area of plate. As the plate gradually plugs up, the flow rate per unit area increases because the flow rate of the gases is maintained essentially constant by the mass flow controllers. The resulting upward shift in the distributor characteristic, pressure drop versus gas flow rate, will result in an error in the computation of the bed pressure drop by the subtraction procedure. The error will be an over estimate of the bed pressure drop, resulting in a rosier picture that shows a lesser extent of channeling than that which really exists.

Heretofore, prior art techniques for monitoring the fluidity of a fluidized bed have been deficient.

SUMMARY OF THE INVENTION

The present invention provides a method for detecting the fluidity of particles in a vertically extending bed of fluidized particles. The particles are confined within a vertically oriented container and upwardly flowing gases are distributed into a bottom portion of the container for fluidizing the particles. An electric charge is generated on the particles. The bed is provided with electrically conductive means which contact the particles during fluidization and discharge the charge on the particles for creating an electrical current in response to particle movement. The flow of electrical current from the electrically conductive means is detected for indicating the fluidity of particles.

In a preferred embodiment, several conductive strips are placed in the fluid bed in contact with the moving particles. The electrical current which passes through the conductive elements to a ground is monitored as a measure of bed fluidity. Enhanced safety, ease of operation, and accuracy may result from detecting bed fluidity in this manner.

When a difficult to fluidize Geldart Class C material, such as a phosphor, is fluidized with varying amounts of a fluidizing aid, measurement of the electrical current results in enhanced monitoring of the fluidity of the bed. This is achieved as evidenced by experimental results.

Disclosed herein is a technique of measuring bed fluidity by monitoring the current flowing to ground through a set of conductive strips attached to the wall of a fluid bed. The particles are charged due to triboelectrification when they rub against the dissimilar material that is the wall of the fluid bed. The charge on the particles is discharged when they contact the conductive strips on the wall. The flow of this charge to ground constitutes the current which is monitored. The more fluid the bed, the larger is the downward flux of particles, the higher is the rate of charge accumulated by the particles, and the greater is the current to ground. This current, also referred to as the wall current in this application, can, therefore, be used to track changes in fluidized bed mobility as a function of time and processing conditions. In addition, this current peaks when the bed fluidity is a maximum.

In order to correlate the wall current with bed fluidity, the bed expansion and elutriation loss were also measured within a bed of phosphor particles containing very fine aluminum oxide C (AOC) particles as an additive. It is known in the industry that very small, about 20 nm or smaller, aluminum oxide C particles can work as a fluidizing aid for cohesive materials, like phosphors. The concentration of the additive at which the bed expansion reaches a local maximum was noted. The additive loading at which the elutriation loss exhibits a peak is found to coincide with the former concentration. The bed mobility is, therefore, highest at this concentration of the fluidizing aid. It is found that the wall current also peaks at tis very same concentration of the fluidizing aid.

According to the experimental results, the peak wall current correlates with the peaks in both the bed expansion and elutriation loss. Since the latter parameters are a joint gauge of bed mobility, this proves that the current generated is a good measure of bed fluidity. Monitoring the current yields valuable information on changes in bed mobility as a function of processing condition and time. By overcoming the deficiencies described above of existing methods, the present invention provides an enhanced method of measuring the fluidity of a fluid bed.

BRIEF DESCRIPTION OF THE DRAWINGS

The invention will become more readily apparent from the following exemplary description in connection with the accompanying drawings, wherein.

DETAILED DESCRIPTION

The present invention provides a method for detecting the fluidity of particles in a vertically extending bed of fluidized particles. The particles are confined within a vertically oriented container and upwardly flowing gases are distributed into a bottom portion of the container for fluidizing the particles. The pressure of gas in a gas source which communicates with the bottom portion for the upward flow of gas is preferably adjustable.

Generally, the vertically oriented container comprises a vertically oriented wall with a gas permeable bottom portion extending transverse to the vertical walls for the upward flow of gas therethrough. The gas permeable member is connected to a source of gas under pressure which is delivered to the bottom portion which is in the form of a plenum.

During the process of fluidization, particles of powder come in contact with the wall. This contact is characterized by a sliding action along the wall, of the downward moving particles. These descending particles along the wall form a part of the downward flux of material in a fluidized bed. The downward flux as well as the inner ascending flux of particles are a consequence of the hydrodynamics of fluidized beds (see Kunii and Levenspiel, *Fluidization Engineering*, Krieger Publishing, 1977), and increase with the superficial gas velocity. The latter is defined as the ratio of the volumetric flow rate of fluidizing gas to the open cross sectional area of the fluid bed.

When two dissimilar insulating materials rub against each other, triboelectrification results. Triboelectrification refers to the transfer of electronic charge between these materials. In the particular case presented in this invention, the glass wall and the descending phosphor particles along the wall constitute the two dissimilar entities. Due to the frictional contact between these materials, the glass and the phosphor particles become charged. In order to maintain charge neutrality, the number of electrons lost by one entity is numerically equal to that gained by the other. In other words, triboelectrification results in both a positively and a negatively charged entity. While a particular phosphor may be negatively charged, and the glass therefore positively charged, when fluidized in a glass walled fluid bed, it is also possible to have a different phosphor which when fluidized will be positively charged with a negatively charged glass wall. The concept presented in this invention is NOT limited to a particular polarity of the phosphor when fluidized.

While a glass walled vessel has been used as the vertically oriented container for the fluidized bed in this invention, any suitable insulating material with a different triboelectric characteristic than the powder being fluidized may be used. This will serve to charge the powder particles. Preferably the insulating material comprises the vertically oriented container, although it is contemplated that other insulating structures may be introduced into the container for contacting the powder. Preferably the insulating material is an abrasion resistant insulating material. Preferred materials are ceramic materials. In a preferred embodiment, the particles comprise phosphor particles. The relative triboelectric characteristics of the particles and the insulating structure may be determined by methods known in the art. Generally, the greater the difference in triboelectric properties, the larger will be the charge on the particles, resulting in an increased current flow when the particles are subsequently discharged.

For the particular phosphor investigated in this invention, the material develops a negative surface charge when fluidized in a glass walled fluidized bed. For a given number of electrons transferred from the glass wall to a single phosphor particle, it follows that the larger the descending flux of particles, the higher is the rate of charge accumulated on the phosphor particles. Anything which increases the fluidity of the fluidized bed, will increase the descending (as well as the ascending) flux. When these charged particles, during subsequent descents and/or ascents, contact the grounded electrically conductive means, the charge on the particles is bled to ground.

The flow of this charge constitutes a current which is detected for indicating the fluidity of the fluidized bed. The detecting and indicating means may comprise an ammeter. Such an ammeter may include a visual display of current flow or include another device, such as an oscilloscope, to give an indication of current flow. Higher current readings are indicative of greater fluidity. The pressure of the source of the gas may be adjusted in response to said detecting means indicating the fluidity of the fluidized bed. For example, the gas pressure may be increased to compensate for an observed drop in bed fluidity.

It follows from the discussion in the previous paragraphs that anything which increases the bed fluidity will increase the wall current. In addition, the wall current is a quantitative measure of the bed fluidity. Bed fluidity may be increased by an intrinsic decrease in powder cohesiveness (as for example by addition of appropriate amounts of fine Aluminum Oxide C), by increasing the gas pressure, hence the superficial gas velocity, or by changing the spatial distribution of fluidizing gas in the fluid bed. Phenomena like agglomeration and loss of fluidizing aid will reduce the bed mobility and reduce the wall current.

The grounded electrically conductive means, referred to earlier, preferably comprises a plurality of metal elements. Preferred metal elements include conductive elements which do not contaminate phosphor particles. Such elements comprise aluminum, nickel, copper or alloys thereof which may be in the form of strips, so as to increase the area of contact with the phosphor particles. Although an increased area enhances the contact with the particles, the metal elements are preferably arranged so as not to interfere with the movement of the powder. A preferred location for the conductive elements is an arrangement closely adjacent the vertically oriented walls of the container, so as not to interfere with powder movement.

The electrically conductive means is preferably electrically isolated from the insulating material. When the electrically conductive elements are closely adjacent the vertically oriented walls of the container, the strips are preferably isolated from the wall by an insulating material. Such electrical isolation may be provided by backing the strips with an electrically insulating layer containing adhesive. If the electrically conductive means is in the form of self-supporting rods or strips, the rods or strips may be conveniently spaced from the insulating wall.

It is worth noting, that during the fluidization of phosphors in a glass container, if the positive charge on the insulated material viz. the glass wall were to survive for a time scale significantly greater than the average circulation time of a phosphor particle, then the wall current would rapidly drop to zero. This is because the charge on the particles is due to fresh charge transferred from the glass wall during every descent. The physics of electrostatics does not favor transfer of additional electrons to the phosphor particles from an already positively charged wall. Several mechanisms may be responsible for bleeding off the charge accumulated on the glass wall. As an example, small amounts of moisture in the fluidizing gas may neutralize the charge on the glass. This mechanism will not destroy the charge on the particles because the surface area of the particles is orders of magnitude greater than that of the glass. While the inventors do not wish to be bound by an explanation of one or more of these mechanisms, the fact remains that conditions exist which maintain the wall current, as evidenced by the information presented in this application.

Disclosed herein is a technique of measuring bed fluidity by monitoring the current flowing to ground through a set of conductive strips attached to the wall of a fluid bed. The particles are charged due to triboelectrification when they rub against the dissimilar material that is the wall of the fluid bed. The charge on the particles is discharged when they contact the conductive strips on the wall. The flow of this charge to ground constitutes the current which is monitored. The more fluid the bed, the larger is the downward flux of particles, the higher is the rate of charge accumulated by the particles, and the greater is the current to ground. This current can, therefore, be used to track changes in fluidized bed mobility as a function of time and processing conditions. In addition, this current peaks when the bed fluidity is a maximum.

EXAMPLE

Bed fluidity was studied using a zinc orthosilicate phosphor, GTE type 2285, with a particle density of 4.107 g/cc as measured by a pycnometric technique. The specific surface area based mean diameter of the powder 5 was 4.67 microns, while the volume based mean diameter was 11.55 microns. The fluidizing aid was AOC with a BET surface area of 82 $m^2/g$ AOC is an aluminum oxide powder which functions as a fluidizing aid for phosphors in the lighting industry. The dominant phase in AOC is gamma alumina, and the primary particle size of the material is about 20 nm.

Ten samples, SRI through SR10, were prepared by V-blending 3 kg lots of the phosphor with varying amounts of AOC. The following concentrations of AOC, expressed as a percentage of the phosphor mass, were used in these samples: 0.0, 0.025, 0.05, 0.1, 0.2, 0.35, 0.55, 0.8, 1.0 and 1.1. The mixing of the two materials was conducted for 30 minutes with the activation of an exciter bar in the blender.

Figure 1:
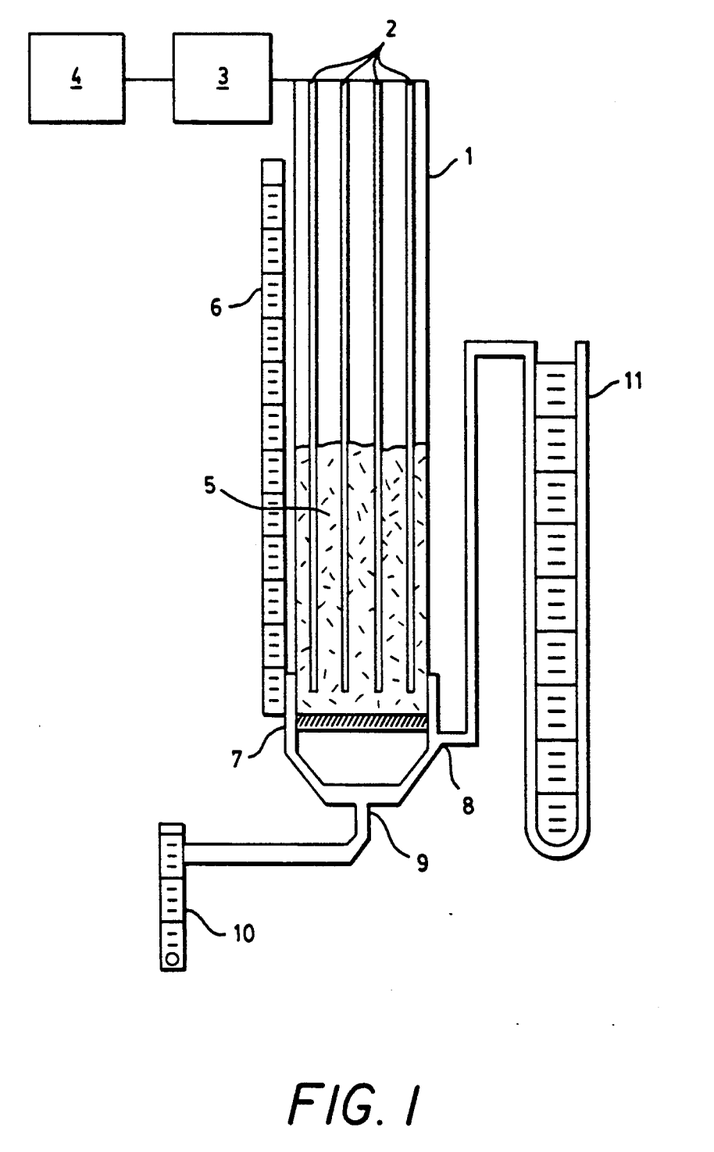
FIG. 1 is a schematic of the fluidized bed apparatus used in connection with the process of the present invention.

A schematic of the invention is shown in FIG. 1. As conductive elements, eight 0.56 cm wide copper strips 2 with adhesive backing were attached symmetrically on the inside of a 10.16 cm ID and 86.4 cm high Pyrex tube 1. The backing electrically isolated the strips 2 from the tube 1. The strips 2 did not contact the 5 micron porosity and 0.157 cm thick stainless steel distributor plate 7 which was gas permeable. At the top of the tube 1, the copper strips 2 were electrically connected to a Keithley picoammeter 3 which delivered a signal to a Tektronix 7854 oscilloscope 4 which served as the indicator means for measuring the current in amperes.

The plenum chamber was constructed of PVC and silicone rubber was used to make the necessary seals. The chamber consisted of a 2.54 cm high straight section above a conical section with a cone angle of 45. and a frustum height of 3.175 cm. A one meter metal ruler 6 was taped to the outer wall of the tube 1 to provide a reading of the bed height. Air was fed to the bottom of the plenum chamber at inlet 9 through a 0.95 cm ID Tygon tube, the flow rate being read off a rotameter 10. A manometer is shown at 11. The observed flow rate was corrected for the small deviation of the rotameter downstream pressure from atmospheric conditions. A pressure tap is provided at 8.

Several runs were conducted for a particular loading of AOC in the phosphor. Prior to the first run for a sample, the mass of powder 5 being fed to the Pyrex tube 1 was weighed. The mass of material in the bed at the end of the last run was also measured to determined the loss due to elutriation. The expanded bed height and time averaged wall current were also recorded.

Detailed statistical analysis of the data was performed using ANOVA and the Tukey's Post Hoc Test. The former indicates whether detectable differences exist between the various AOC treatments. It does not, however, tell which of the AOC treatments are different from each other. The Tukey's Post Hoc Test makes that possible by conducting all possible pairwise comparisons between the subgroups.

Bed Expansion

Figure 2:
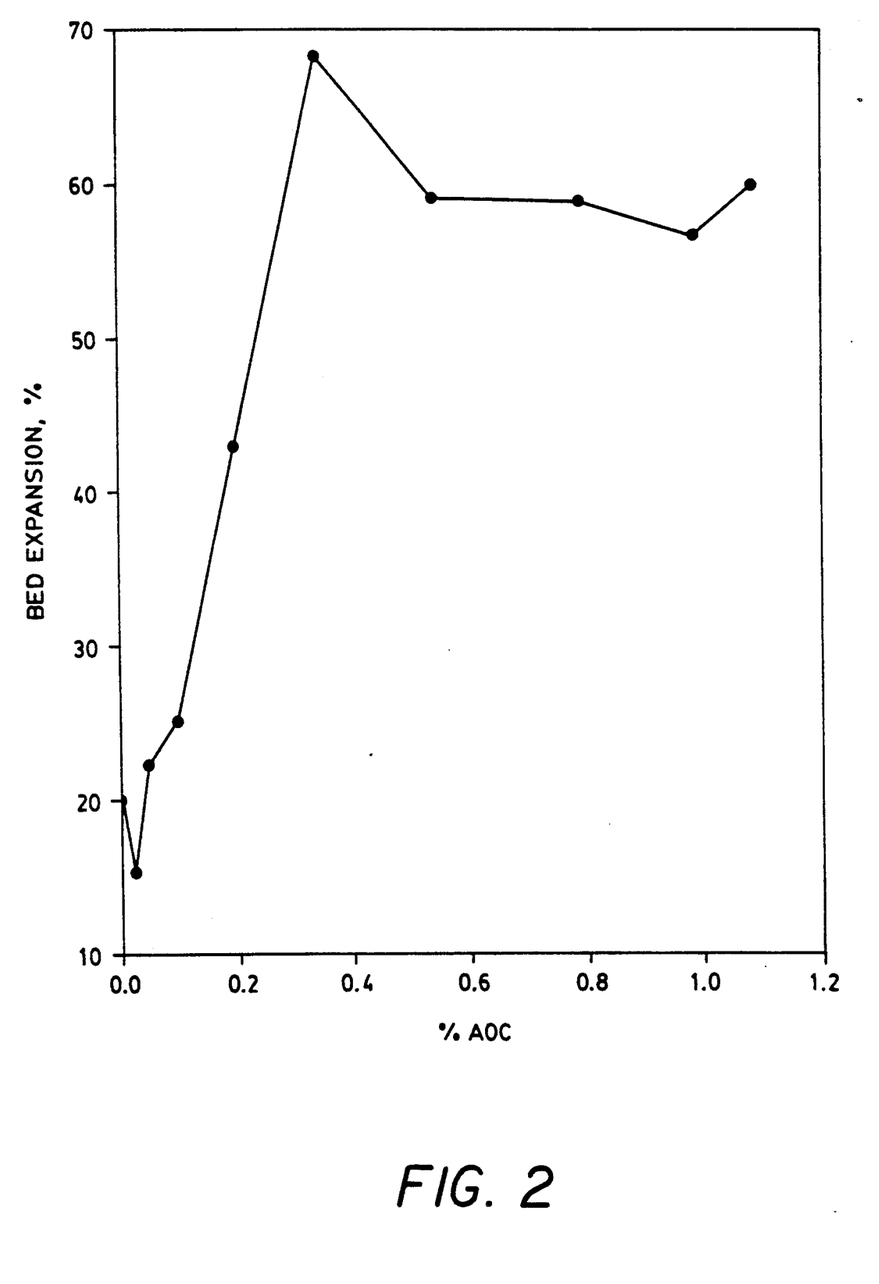
FIG. 2 is a graph showing mean bed expansion as a function of the AOC level in the phosphor fed to the fluidized bed apparatus.

The expanded bed height at the maximum gas superficial velocity was divided by the static bed height to yield a normalized bed expansion. The mean bed expansion is shown in FIG. 2 as a function of the AOC level in the phosphor fed to the Pyrex tube 1.

Statistical hypothesis testing indicates that there is insufficient evidence, at the 5% significance level, to reject the null hypothesis that the mean bed expansion is the same over an AOC concentration range of 0.55% to 1.1%. The analysis also indicates that there is no detectable change in bed expansion over an additive range of 0 to 0.1%. Detectable differences in bed expansion are manifested, as the AOC loading is varied from 0.1% to 0.55%. The highest mean bed expansion is realized at an AOC loading of 0.35%, indicating that maximum bed fluidity probably occurs at this concentration of the fluidizing aid.

Elutriation Loss

The initial charge of powder 5 fed to the fluid bed, for a given AOC level, experiences a gradual loss in mass over the course of the runs. This is attributed to elutriation. The highest superficial velocity in the experiments was about 8 cm/s. Parameters like minimum fluidization velocity and terminal velocity cannot be applied to fluidization of Geldart type C materials, like this phosphor. This is because inter-particle forces, which are practically absent in Group B and A materials, play a major role in the hydrodynamics of these fine particles.

Figure 3:
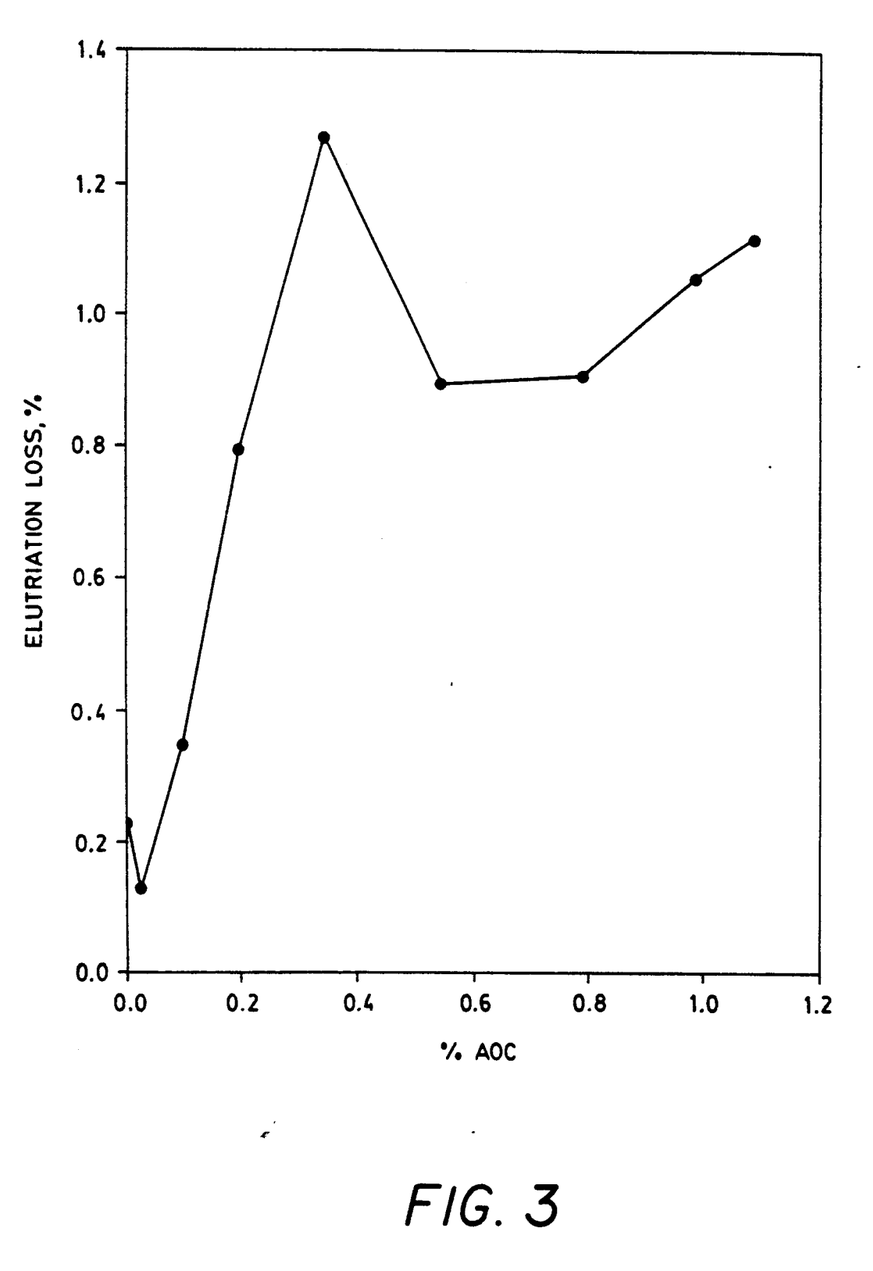
FIG. 3 is a graph showing the percentage of initial bed mass lost due to entrainment.

The percentage of initial bed mass lost due to entrainment, expressed on a per run basis, is shown in FIG. 3. It is important to note that this loss, for a particular concentration of AOC, is a cumulative one resulting from the imposition of gradually increasing superficial velocities over every run. Since the gas flow rate settings were practically identical for all the runs and the duration of a particular flow setting varied very little from run to run, it may be concluded that the elutriation loss shown in FIG. 3 reflects primarily the effect of AOC.

It is observed that the elutriation loss peaks at an AOC level of 0.35%. This knowledge, when coupled with the bed expansion information, leads to the conclusion that the peak bed mobility occurs at a fluidizing aid concentration of 0.35%.

SEM micrographs indicate that fluidization does not preferentially strip the much smaller AOC particles from the larger phosphor particles in the bed. Considerable AOC still remains attached to the bed phosphor at the end of the last run. The presence of AOC on the surface of the elutriate is also evident.

Generated Current

Figure 4:
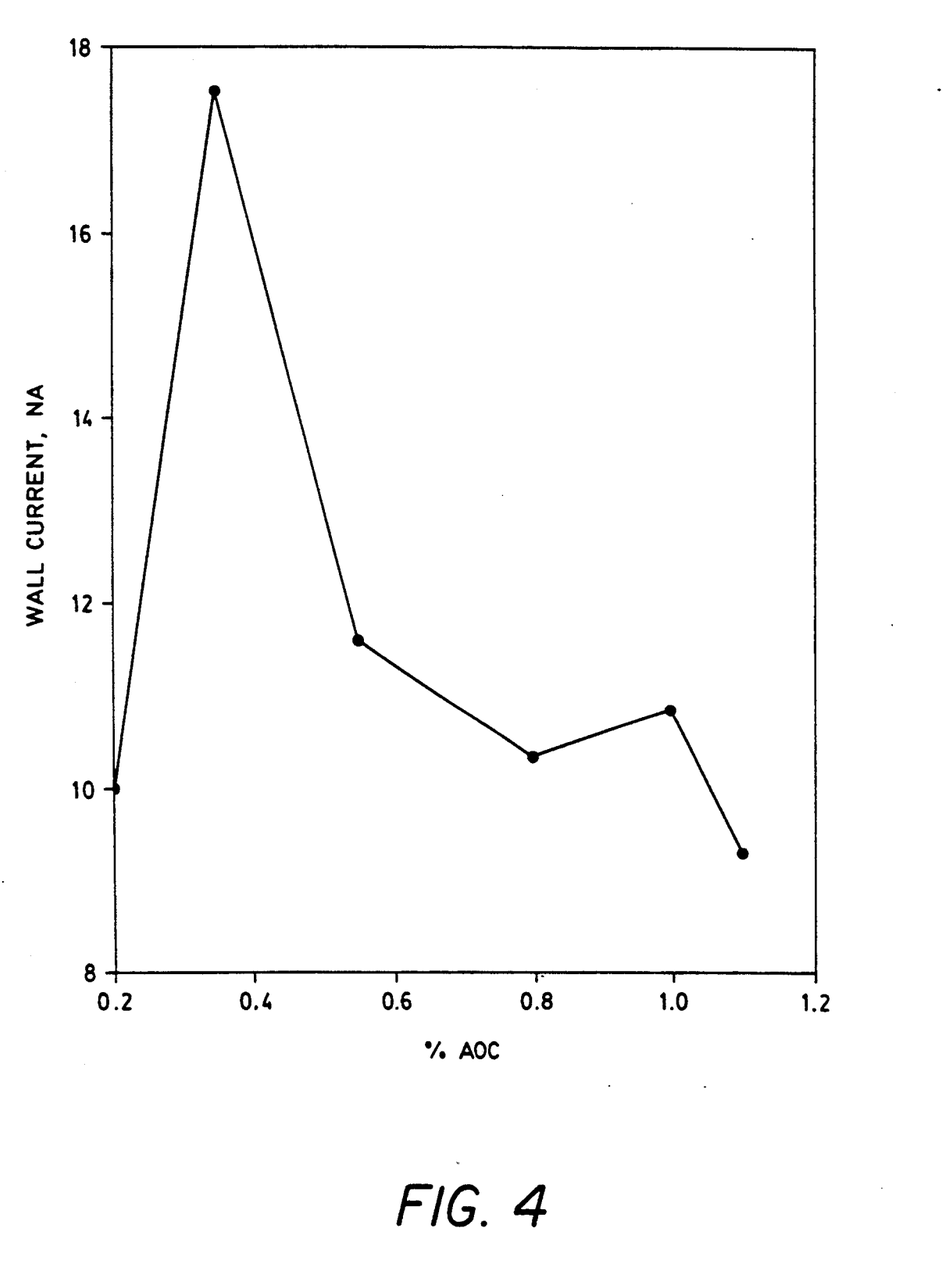
FIG. 4 is a graph showing the effect of AOC on the magnitude of the wall current.

The current generated by the particles 5 contacting the strips 2 is measured by the detecting means in the form of a picoammeter 3. The picoammeter 3 has an indicator that may be visually read. The effect of AOC on the wall current is shown in FIG. 4. No current is detected below an AOC level of 0.11%. The mean wall current for an AOC level of 0.35% is the highest and is detectably different from the mean currents for all the other treatments.

This AOC level is identical to that at which the bed expansion and the elutriation loss also exhibit local maximum. In other words, the wall current peaks when the bed has the highest degree of fluidity.

Figure 5:
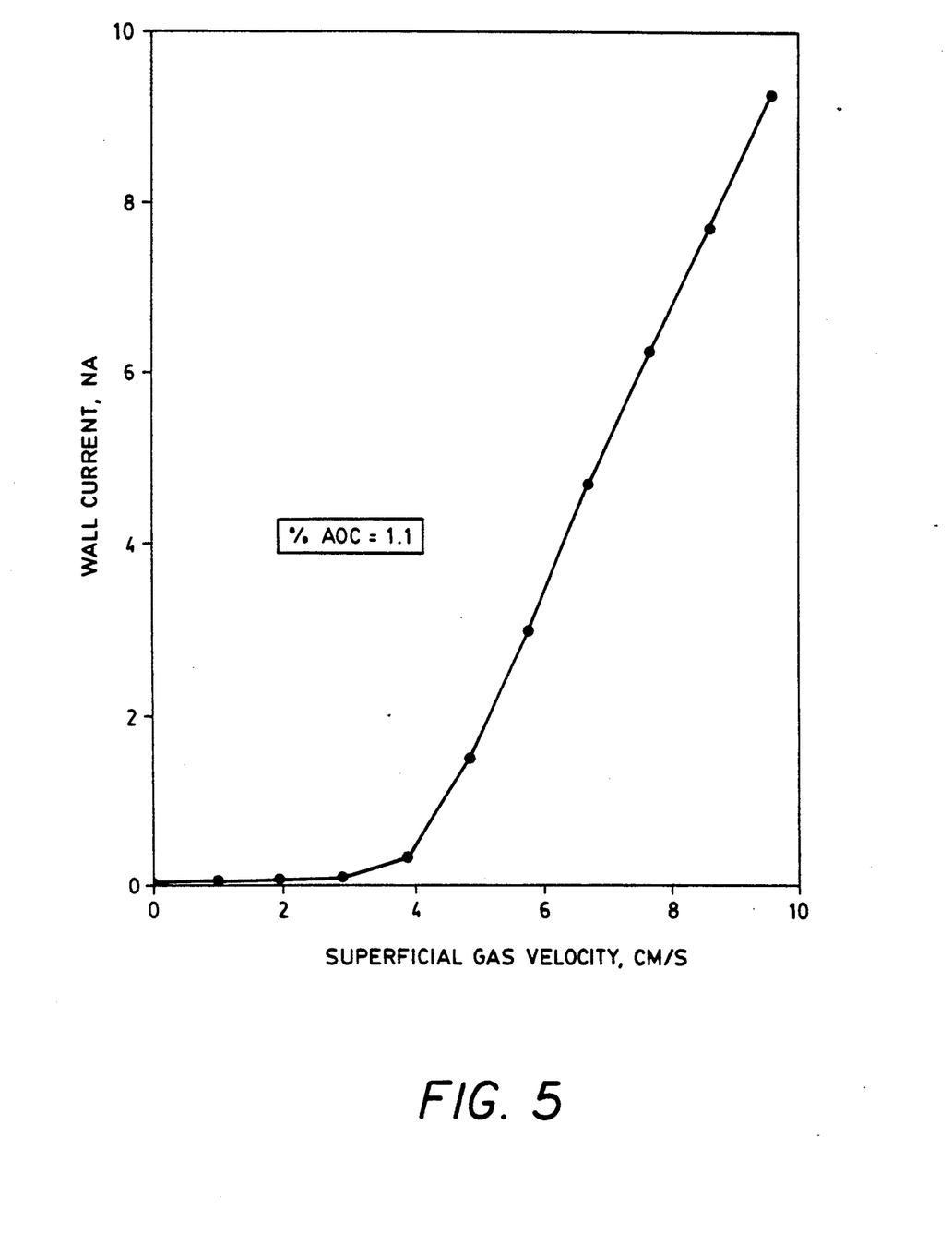
FIG. 5 is a graph showing the effect of gas superficial velocity on the magnitude of the wall current.

This invention has found that the peak wall or generated current correlates with the peaks in both the bed expansion and elutriation loss. It has been stated earlier that the latter parameters are a joint gauge of bed mobility (used interchangeably with fluidity). The wall current can, therefore, rightly be used as a measure of bed fluidity. The correlation of the wall current with bed mobility is further substantiated by the increase in the current with gas superficial velocity. FIG. 5 shows this effect very clearly. A higher gas velocity results in an increase in the solids flux, and as has been described in the "Detailed Description" section, this in turn should produce a higher wall current.

Monitoring of the wall current can yield valuable information on changes in bed fluidity as a function of processing condition and time. By overcoming the deficiencies described in the "Background" section of this application this invention makes a positive contribution to the general field of fluid bed technology and allied fields including, but not necessarily limited to, powder CVD.

We claim:

1. A method for detecting the fluidity of particles in a vertically extending bed of fluidized particles confined within a vertically oriented container wherein upwardly flowing gases are distributed into a bottom portion of said container for fluidizing the particles, said method comprising generating an electric charge on said particles, providing said bed with electrically conductive means for contacting particles during fluidization and operable for discharging said charge on said particles for creating an electrical current through said electrically conductive means in response to particle movement, and detecting said electrical current through said electrically conductive means for indicating the fluidity of particles.

2. A method for detecting the fluidity of particles in a vertically extending bed of fluidized particles according to claim 1 comprising generating an electric charge on said particles by contacting said particles with an insulating material having a different triboelectric value.

3. A method for detecting the fluidity of particles in a vertically extending bed of fluidized particles according to claim 2 wherein said insulating material comprises said vertically oriented container.

4. A method for detecting the fluidity of particles in a vertically extending bed of fluidized particles according to claim 3 wherein said vertically oriented container comprises an abrasion resistant insulating material.

5. A method for detecting the fluidity of particles in a vertically extending bed of fluidized particles according to claim 3 wherein said vertically oriented container comprises a vertical wall for confining said fluidized particles, said electrically conductive means being electrically isolated from said vertical wall.

6. A method for detecting the fluidity of particles in a vertically extending bed of fluidized particles according to claim 5 wherein said electrically conductive means comprises a plurality of metal elements.

7. A method for detecting the fluidity of particles in a vertically extending bed of fluidized particles according to claim 6 wherein said metal elements are selected from the group consisting of aluminum, nickel, and copper.

8. A method for detecting the fluidity of particles in a vertically extending bed of fluidized particles according to claim 7 wherein said particles comprise phosphor particles.

9. A method for detecting the fluidity of particles in a vertically extending bed of fluidized particles according to claim 8 including a source of gas under pressure communicating with said bottom portion for the upward flow of gas, said pressure of said gas being adjustable.

10. A method for detecting the fluidity of particles in a vertically extending bed of fluidized particles according to claim 9 wherein said detecting said electrical current comprises measuring the electrical current, and said method comprises adjusting the pressure of said gas source in response to said electrical current being measured.

11. A method for detecting the fluidity of particles in a vertically extending bed of fluidized particles according to claim 10 wherein said measuring the electrical current indicates the fluidity of said bed wherein a decrease in current flow is indicative of a decrease in bed fluidity.

12. A method for detecting the fluidity of particles in a vertically extending bed of fluidized particles according to claim 11 comprising increasing said gas pressure in response to a lesser current flow.

13. A method for detecting the fluidity of particles in a vertically extending bed of fluidized particles according to claim 1 wherein said vertically oriented container comprises a vertically oriented wall and said bottom portion comprises a gas permeable member extending transverse to said vertically oriented wall for the upward flow of gas therethrough, said gas permeable member being connected to a source of gas under pressure, changing said pressure in said source of gas under pressure in response to an indication of the fluidity of said particles.

14. A method for detecting the fluidity of particles in a vertically extending bed of fluidized particles according to claim 13 wherein said detecting said electrical current through said electrically conductive means for indicating the fluidity of particles comprises measuring said electrical current with an ammeter.

* * * * *